(12) United States Patent
Corazza et al.

(10) Patent No.: US 12,311,068 B2
(45) Date of Patent: May 27, 2025

(54) UV DISINFECTION BOX SYSTEM

(71) Applicant: SAES GETTERS S.P.A., Lainate (IT)

(72) Inventors: Alessio Corazza, Como (IT); Luca Mauri, Cesano Maderno (IT); Marco Filippo Batavia, Lucca (IT); Ginevra Della Porta, Milan (IT); Arianna Papadia, Milan (IT)

(73) Assignee: SAES GETTERS S.P.A., Lainate MI (IT)

( * ) Notice: Subject to any disclaimer, the term of this patent is extended or adjusted under 35 U.S.C. 154(b) by 0 days.

(21) Appl. No.: 18/711,228

(22) PCT Filed: Nov. 28, 2022

(86) PCT No.: PCT/EP2022/083534
§ 371 (c)(1),
(2) Date: May 17, 2024

(87) PCT Pub. No.: WO2023/094669
PCT Pub. Date: Jun. 1, 2023

(65) Prior Publication Data
US 2024/0325578 A1   Oct. 3, 2024

(30) Foreign Application Priority Data
Nov. 29, 2021   (IT) .......................... 102021000030089

(51) Int. Cl.
*A61L 2/10*   (2006.01)
(52) U.S. Cl.
CPC ............. *A61L 2/10* (2013.01); *A61L 2202/11* (2013.01); *A61L 2202/122* (2013.01); *A61L 2202/16* (2013.01)

(58) Field of Classification Search
CPC ... A61L 2/10; A61L 2202/11; A61L 2202/122
See application file for complete search history.

(56) References Cited

U.S. PATENT DOCUMENTS 9,657,177 B1 * 5/2017 Pringle ................ C09D 127/16
2008/0265179 A1   10/2008 Havens et al.
(Continued)

FOREIGN PATENT DOCUMENTS

CN          212220851 U      12/2020

OTHER PUBLICATIONS

International Search Report and Written Opinion issued Mar. 17, 2023 in PCT/EP2022/083534, 12 pages.

*Primary Examiner* — Jennifer Wecker
*Assistant Examiner* — Brady C Pilsbury
(74) *Attorney, Agent, or Firm* — Element IP, PLC

(57) ABSTRACT

A box-shaped UV disinfection system (100) comprises a plurality of internal UV sources (121, 122, 131, 132, 141, 142) disposed on at least two of its walls (120, 130, 140) that are adjacent to each other, all of the internal wall surfaces having a reflectance higher than 80% and preferably higher than 87% in the wavelengths range between 250 and 350 nm, and a UV-transmitting support (101) that has at least a 70% UV transmittance in said wavelengths range and is located at a suitable minimum distance from the base wall (110), the UV sources (131, 132, 141, 142) disposed on at least one of its walls (130, 140) being inclined towards the base wall (110) with an angle comprised between 5° and 30°. Such a system has improved characteristics in terms of efficiency and in a preferred embodiment also has better portability.

20 Claims, 6 Drawing Sheets

(56) References Cited

U.S. PATENT DOCUMENTS

| | | |
|---|---|---|
| 2013/0078142 A1 | 3/2013 | Gordon |
| 2015/0297768 A1 | 10/2015 | Bettles et al. |
| 2018/0221521 A1* | 8/2018 | Shur .................. A61L 2/00 |
| 2018/0236115 A1* | 8/2018 | Yerby .................. A61L 2/24 |
| 2019/0290074 A1 | 9/2019 | Chen |
| 2021/0299302 A1 | 9/2021 | Mullen et al. |
| 2021/0308296 A1 | 10/2021 | Cook et al. |
| 2021/0369015 A1* | 12/2021 | Nevitt .................. A61L 2/10 |
| 2021/0393835 A1* | 12/2021 | Rosenblat .............. A61L 2/26 |
| 2022/0047751 A1* | 2/2022 | Carbone .............. B65B 55/16 |
| 2022/0054674 A1* | 2/2022 | Gadotti Martins ..... A61L 2/202 |
| 2022/0135280 A1* | 5/2022 | Pozzato .............. B65D 5/322 |
| | | 250/455.11 |
| 2022/0160911 A1* | 5/2022 | Lu .................. A61L 2/24 |
| 2022/0168456 A1* | 6/2022 | Jones .................. A61L 2/10 |
| 2022/0347326 A1* | 11/2022 | Ho .................. A61L 2/10 |
| 2023/0338594 A1* | 10/2023 | Maier .............. B60H 3/0078 |

* cited by examiner

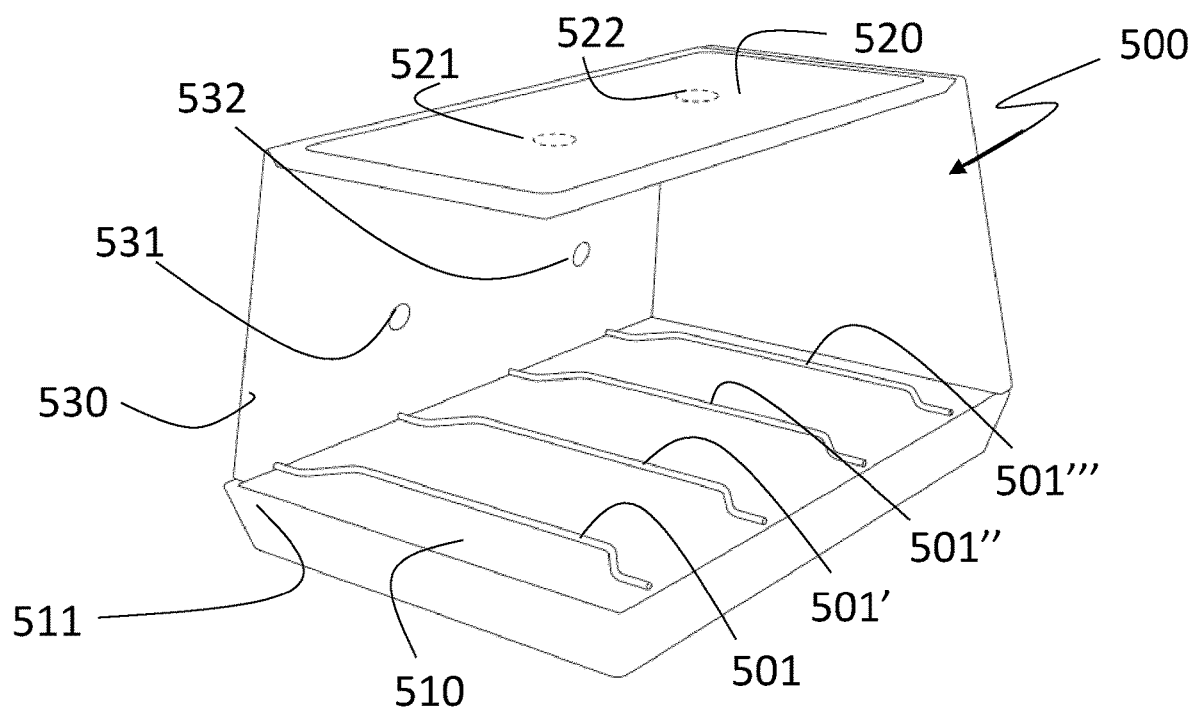
Fig.5A
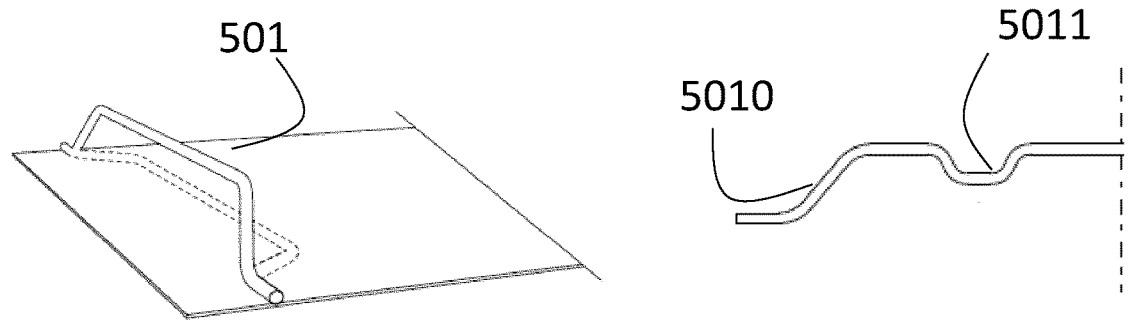
Fig.5B
Fig.5C

UV DISINFECTION BOX SYSTEM

The present invention is inherent to a UV disinfection box system with improved characteristics in terms of efficiency and in a preferred embodiment with improved portability.

The use of UV radiation for items disinfection in compact form such as "boxes" where the items to be disinfected are placed inside is quite widespread and known since a long time, as for example described in the German application DE3044181, or US application US20070274879, both using lamps as UV sources.

These devices have undergone continuous improvements, for example with regards to preferred UV sources that present a main emission in the so called UV-C region, such as for example described in the international application WO2021101431 describing the heightened sterilizing effect achieved by combining UV sources having different UV wavelength emission spectra, more specifically a first UV source with a first wavelength range having an upper limit extending up to at least 270 nm, and a second UV source with a second wavelength range having a lower limit extending down to at least 270 nm and an upper limit extending up to at least 320 nm. Also this patent application discloses a series of suitable UV sources for UV disinfection boxes, such as low pressure mercury lamps, UV LEDs or UV chips. UV chips are less common with respect to the other two sources, but preferable as they are cold sources not requiring heat shielding or systems for thermal management of the generated heat. More details for this type of source can be found in the international application WO2018106168.

One of the aspects to consider with UV disinfection boxes is how to maximize the pathogenic microorganisms killing action of the sources, especially when the purpose is the disinfection of 3D objects (such as keys, cellular phone, wallet, crockery and cutlery, glasses, containers, pacifiers, baby bottles, toys, etc.), in order to minimize the number of sources used and/or the disinfection treatment time, for cost-related issues and/or for process efficiency. More sources and/or longer process times have a negative impact on power management aspects and this is an issue for "hot" UV sources with regards to thermal management, as for example addressed via heat-spreaders in US patent application US20210085812, whereas with cold sources there are issues to consider with systems not powered via connection to the voltage mains, such as battery-operated ones or solar panel-assisted systems.

Moreover, there is also the need to maximize the efficiency of the box while considering the impact on the object to be sanitized. In fact, it is known that repeated UV exposure, especially to UV-C which is the most effective germicidal radiation, can lead to plastic degradation: see for example the article "Damage to Common Healthcare Polymer Surfaces from UV Exposure" by Peter Teska et al., published on "Nano LIFE VOL. 10, NO. 03, 2020, or the paper "Ultraviolet light accelerates the degradation of polyethylene plastics", by Mustafa Doğan, published on Microsc. Res. Tech., 2021 November; 84(11):2774-2783.

Purpose of the present invention is to provide a novel UV box system with improved performances with respect to the ones of the prior art with particular regard to the placement and effectiveness of the employed UV sources. The invention concerns a UV disinfection box system having at least a displaceable wall, wherein all of the UV box internal wall surfaces have a reflectance higher than 80%, and preferably higher than 87%, in the wavelengths range between 250 and 350 nm, said UV disinfection box system comprising a plurality of discrete UV sources that are disposed within the UV box on at least two of its walls that are adjacent to each other, and not present on at least one of the UV box walls, the UV box further comprising an internal UV-transmitting support having at least a 70% UV transmittance and disposed at a minimum distance d1 from a base wall and at a maximum distance d2 from an opposite upper wall, wherein $0.1 \leq d1/(d1+d2) < 0.5$, preferably $0.15 \leq d1/(d1+d2) \leq 0.4$.

Examples of UV disinfection box systems of this kind, as recited in the preamble of claim 1, are found in US 2013/078142 and US 2008/265179, from which the present invention is distinguished by the fact that the discrete UV sources disposed on at least one of the walls are inclined towards the base wall with an angle comprised between 5° and 30°.

As will be evident from the following description and schematic representation of preferred embodiments, the term "adjacent walls" is to be intended and interpreted as walls having a common border.

The preferred way to characterize the UV reflectance as well as the UV transmittance is by means of measurement in an integrating sphere: as outlined in the summer 2010, vol. 5 Talk letter, by Shimadzu, this allows to properly evaluate also the so-called diffused reflectance contribution.

The inventors have found that with the above-described solution, thanks to the synergistic effect of all the elements described above, it is possible to irradiate all the surfaces of an object placed in the box with a high enough UV irradiance, even though one or more of the box walls do not present discrete UV sources (in a preferred embodiment one of the box walls without UV sources is its base). This allows with a single disinfection cycle usually spanning between 30 seconds and 6 minutes, most typically between 40 seconds and 3 minutes, to achieve with low power energy a proper disinfection at a pathogenic microorganisms inactivation level of at least 99.9% on all the object surfaces exposed to inner volume V, also of the surfaces not directly facing the discrete UV sources.

Suitable UV sources are UV-C LEDs, UV chips such as those described in the aforementioned international application WO2018106168 and other UV-C mercury-free lamps, such as, for example, UV excimer lamps. The use of UV chips is preferable because they provide a strong inactivation action against bacteria and viruses as a result of the peculiar spectrum having a continuous emission between 250 and 320 nm with a first peak in the range 260-280 nm and a second peak in the region 290-310 nm, with the main intensity peak at about 265 nm. It is possible to have a single discrete UV source that emits UV radiation with both said first and second spectral emission peaks, or a first discrete UV source that emits radiation centered on said first peak and a second discrete UV source that emits radiation centered on said second peak.

The invention will be further illustrated with the help of the following figures, where:

FIG. 5A shows a schematic representation of a UV box interior, whereas FIGS. 5B and 5C are enlarged views of one of its details.

In the above figures, the dimensions and dimensional ratios of the represented elements are not always correct but in some cases they have been altered in order to improve their comprehension, with particular and non-exclusive reference to walls thickness and dimensions of the UV sources with respect to the box walls dimensions. Moreover, elements that are not necessary for the figure comprehension and of common knowledge for a person of ordinary skill in the art, such as electrical connections, electronic components and driving unit of the sources, have not been represented.

Figure 1:
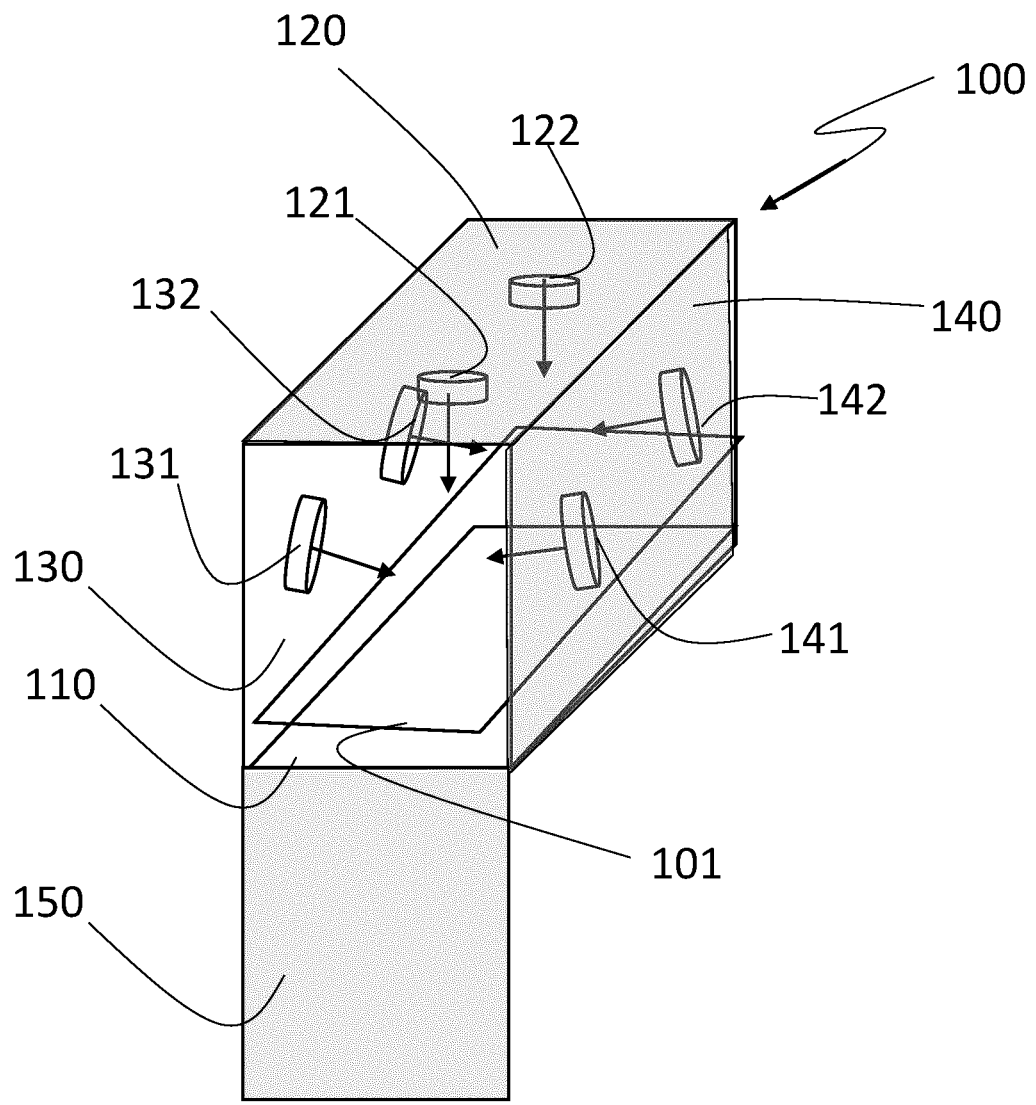
FIG. 1 is a schematic representation of a first embodiment of a UV box according to the present invention.

A schematic representation of a UV box 100 according to a first embodiment is shown in FIG. 1 to have three pairs of discrete UV sources disposed onto the inner surfaces of three walls: UV sources 131 and 132 onto a side wall 130, UV sources 141 and 142 onto an opposite side wall 140, and UV sources 121 and 122 onto the upper wall 120. The other three UV box walls, namely front wall 150, base wall 110 and back wall (not shown) do not have discrete UV sources mounted thereon, and the UV box is shown "open" with the front wall 150 connected only to the base wall 110.

Between the base wall 110 and the upper wall 120 there is present a UV-transmitting support 101, whose positioning is crucial to ensure an efficient irradiation from below of the object to be disinfected. Such positioning is defined by the above-mentioned expression $0.1 \leq d1/(d1+d2) < 0.5$, i.e. it should be between 10% and 50% of the distance between the base wall 110 and the upper wall 120 (i.e. the UV box height), this condition expressing the need for the UV-transmitting support 101 to be at a certain and proper distance with respect to the base wall 110. In this respect, d1 indicates the minimum distance between support 101 and the base wall 110, in case support 101 is slanted and/or does not have a flat shape, and d2 indicates the maximum distance between support 101 and the upper wall 120, in case support 101 and/or the upper wall 120 is slanted and/or does not have a flat shape.

As shown in FIG. 1, the front wall 150, due to the fact that it needs to be displaced/moved to open/close the UV box 100, is preferably without UV sources, as their presence would pose some constraints for their electrical supply. Discrete UV sources 121, 122, have an outgoing UV radiation with the main component orthogonal to the walls on which they are mounted, and with an angular emission distribution of 100° for standard UV chips and 120°-130° for standard UV LEDs.

UV sources 131, 132 disposed onto the first side wall 130 and UV sources 141, 142 disposed onto the opposite side wall 140 are mounted with a certain downward inclination, comprised between 5° and 30°, so that their main emission is not perpendicular to the mounting walls 130, 140 but forms a smaller angle comprised between 85° and 60°, i.e. is oriented towards the base wall 110.

It is noted that it is not necessary for all the discrete UV sources to have an "inclined" emission toward the base wall 110, but this requirement shall be fulfilled by at least all the UV sources mounted onto a wall, preferably a side wall. More preferably, all the discrete UV sources with the exception of those mounted on the upper wall 120 have an inclined emission toward the base wall 110.

Figure 2:
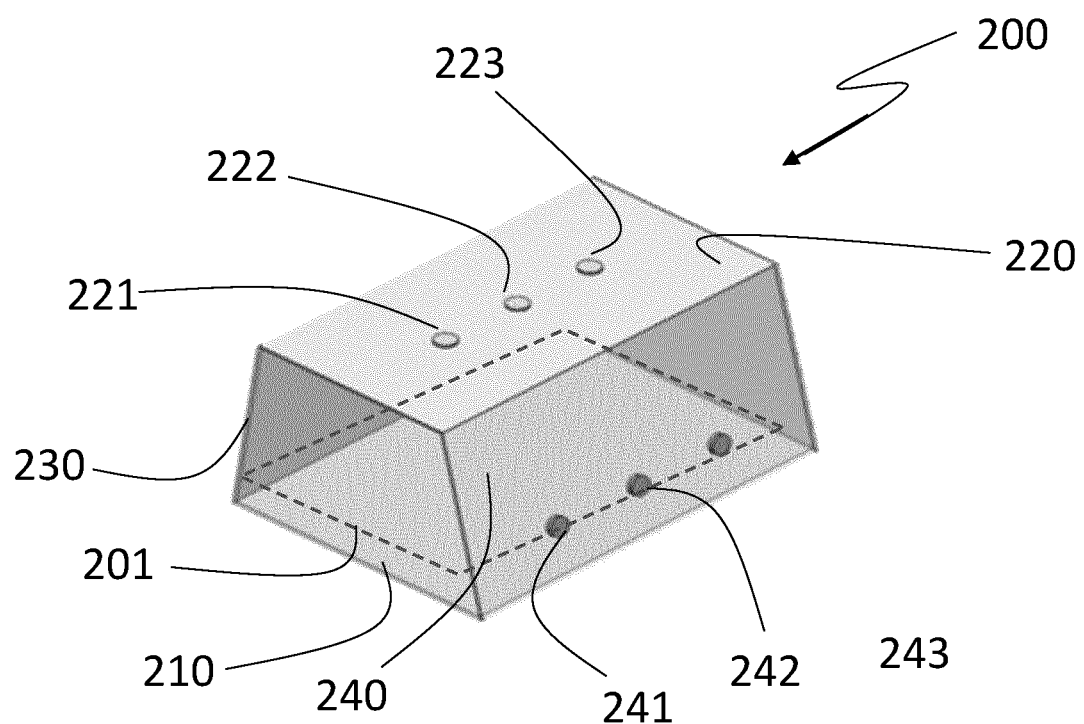
FIG. 2 is a schematic representation of a second embodiment.

An alternate way to achieve the inclined UV emission is shown in the second embodiment of FIG. 2, outlining the structure of a UV box 200 with UV-transmitting support 201 and side walls 230, 240 inclined inwards by virtue of the trapezoidal cross-sectional shape of the UV box, that has the upper wall 220 smaller than the base wall 210. While all UV sources 221, 222, 223 and 241, 242, 243 are mounted parallel respectively to walls 220 and 240 (i.e. with a main emission direction perpendicular to their mounting walls), for UV sources 241, 242, 243 the main emission is inclined towards the base wall 210 due to the inclination of the side wall 240. The inclination angle of the side walls carrying the UV sources with respect to the base wall 210 is comprised between 60° and 85°.

As the side wall 240 fulfills the inclination requirement of the present invention, the side wall 230 could also be perpendicular to the base wall 210 as in the first embodiment, or it could even be inclined outwards if that could be useful for a proper reflection of the UV radiation (in that case the cross-section would be more similar to a parallelogram), even though the preferred configuration is the one represented in FIG. 2, with the side wall 230 mirroring the side wall 240 carrying the UV discrete sources It is important to underline that the UV boxes of the present invention are not limited to a specific number of UV sources or a specific placement over the box walls as long as they fulfill the more general requirements expressed in claim 1. Having said that, the preferred configurations envision the use of six discrete UV sources, in one case distributed evenly on three walls with two sources for each wall (as in the embodiment of FIG. 1), or alternatively distributed evenly on two walls with three sources for each wall (as in the embodiment of FIG. 2). A second preferred configuration envisions the use of four discrete UV sources distributed on three walls, most preferably two sources on the upper wall and one on each side wall.

With regard to the power of such UV sources, the most efficient and low consumption systems present a ratio of the cumulative electric power P of the discrete UV sources to the inner volume V comprised between 0.25 and 0.60 mW/cm$^3$.

Figure 3:
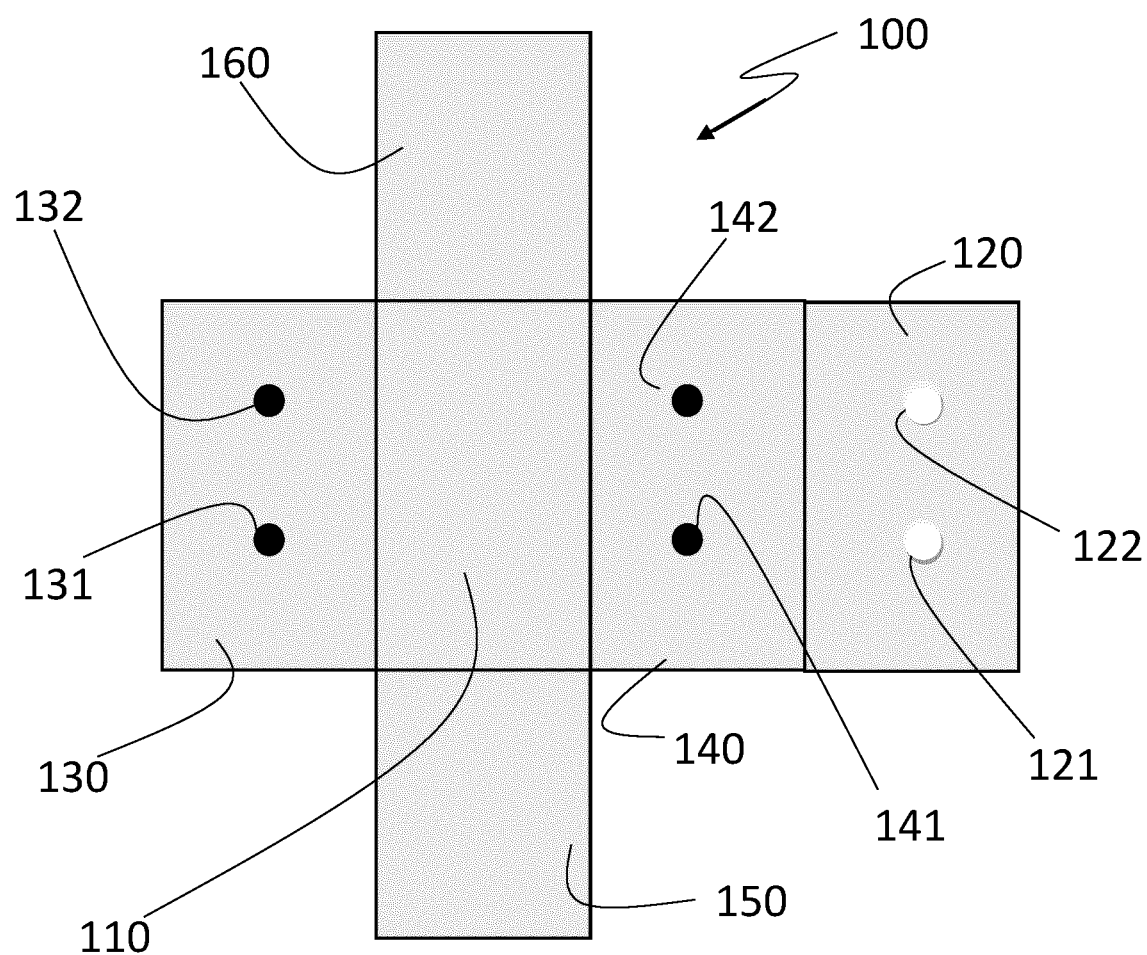
FIG. 3 is a schematic view from above of the first embodiment shown in FIG. 1 in an "unfolded" configuration.
Figure 4:
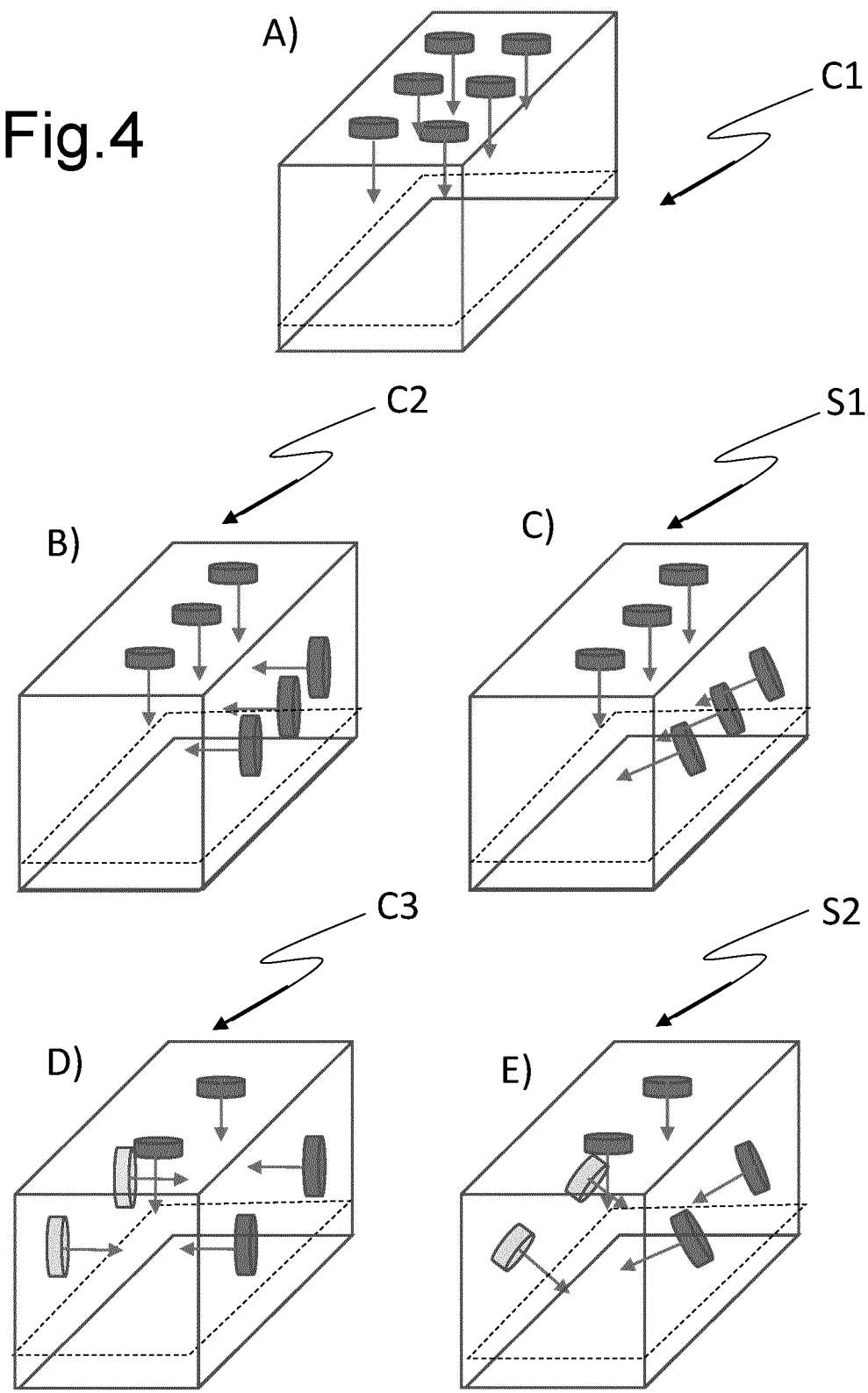
FIGS. 4A-4E show two schematic representations of a UV box configuration according to the present invention as well as three comparative examples, as tested and herein exemplified.

All the UV boxes according to the present invention can be made with a rigid structure with just a movable panel to open and close the box, or alternatively they can be made by foldable/joinable panels, as exemplified in FIG. 3 that represents a view from above in the unfolded condition of the assembled UV box 100 shown in FIG. 1. As already described above, UV sources 131 and 132 are mounted on box panel 130 (first side wall), UV sources 141 and 142 are mounted on box panel 140 (second side wall), UV sources 121 and 122 are mounted on box panel 120 (upper wall), whereas panels 110 (base wall), 150 (front wall) and 160 (back wall) do not present UV sources. Electric connections between the UV sources and the electronic control components and power-driving unit can be arranged on or embedded in the panels.

As shown in the exemplary embodiment of FIG. 5, the electronic control components and power driving unit (as well as any other electrical or logic element) can be located in a container 511 whose upper surface is the base 510 of the UV box 500 or alternatively is attached to the UV box base.

FIG. 3 shows the panels already joined so that the box can be folded into the assembled condition, but they could be totally separated and joined together via suitable adhesive strips, connected or connectable via hinges, or alternately they can present semi-permanent joints so that after a first set up the box walls do not need to be fully separated but they can be folded over. When the panels are unfolded, a compact and tiny structure can be obtained in such a way that the system can be easily stored or transported and readily re-assembled for operation, preferably with a ratio between its inner volume V and the volume of the unfolded box comprised in the range 4-16. The UV discrete sources 131, 132, 141, 142 represented with black circles are inclined with respect to the mounting walls 130, 140, whereas the UV discrete sources 121, 122 represented with white circles are mounted parallel to wall 120 as this will be the upper wall of the UV box, once assembled.

In the case of a UV box with separable walls, those can be stored in a suitable container, containing also the electronic module and its components, in this regards a preferred solution is the container 511 of FIG. 5.

A common feature possessed by all the UV box embodiments according to the present invention is the high reflectance of the inner surface of the UV box walls (i.e. the surface of the walls facing the inner volume V), more specifically such reflectance should be >80% and preferably >87% in the wavelengths range between 250 and 350 nm.

Suitable materials for the UV box inner surfaces are porous fluoropolymer layers, in particular expanded PTFE (e-PTFE) or porous PTFE, specifically Porex Virtek™ (supplied by Porex Corp.) with average UV reflectance of 94% for a 0.75 mm thick layer and of 91% for a 0.5 mm thick layer. Special UV-reflecting aluminium layers have also suitable high UV reflectance (equal to or higher than 90%), e.g. the UV-C Miro Aluminium reflectors by Alanod have UV reflectance higher than 90%, or the Vega UV-C aluminium surfaces with nanometric PVD layers by Almeco have UV reflectance higher than 91%. The above solutions allow to achieve higher UV reflectances, a very important aspect for the minimization of the number of UV sources, and in this regard it is important to underline that standard UV boxes typically use standard Al reflective layers, achieving up to 75% of UV reflectance, as exemplified in the historical reference "Ultra-violet reflecting power of Aluminum and several other metals" by William Weber Coblentz et al., Bureau of Standards Journal of Research, volume 4, page 189 or the more recent paper "Laser-based Surface Modifications of Aluminum and its Alloys" by M. M. Quazi et al., Critical Reviews in Solid State and Materials Sciences, 0:1-26, 2015, with particular reference to its FIG. 1.

Devices based on external light emission for disinfection such as the one described in the US application US20080253941, or a lighting system with disinfection as additional feature, such as described in the US application US20160215941 as well as the international application WO2011049859 rely onto an opposite mechanism (light emission) to achieve disinfection. Whereas another possibility, as described in the Indian application IN202011020635, is to achieve full object exposure to UV radiation through movement/rotation of the UV sources.

Another common feature shared by all the UV box embodiments according to present invention is the UV transmission characteristic of the support for the objects to be disinfected, that shall be at least 70% in the 250-350 nm range. As already outlined with regards to the UV box wall reflectance, also the transmittance can be characterized by means of an integrating sphere.

This effect could be achieved using a UV-transparent material, for example some thin fluoropolymers foils (typically having thicknesses in the range 120-300 μm) with good UV transmission characteristics such as, for example, UV-transparent fluoropolymers like THV (a polymer of tetrafluoroethylene, hexafluoropropylene and vinylidene fluoride) or ETFE (ethylene tetrafluoroethylene). With these exemplary materials it is possible to achieve UV transmission of the support higher than 70%, for example a 0.18 mm thick THV support has a UV transmittance higher than 75%.

Also special thin plates of UV-transmitting synthetic glasses can be usefully employed, but they are less preferred as usually more fragile and sensitive to mechanical shocks. An alternative solution is the use of a netted structure with a void-to-fill ratio comprised between 3 and 200.

The support can be a standalone element sustained by suitable pillars of proper height or can be a flat element to be inserted in suitable grooves in the box inner structure; alternately, the support is hinged onto a side wall to enable its folding for boxes made with foldable/separable panels. In this case, it is also envisioned the possibility to have two half-width supports each hinged onto a wall, such that the assembly of the UV box leads to the formation of the support by bringing together the two half-width supports.

Another preferred solution for the support is illustrated in FIG. 5, showing a perspective view of UV box 500 with the front and right panel removed, having a container 511 coupled to or forming the base wall 510. UV sources 521, 522, 531, 532 are respectively disposed onto two adjacent walls, namely a top wall 520 and a side wall 530. The bottom container 511 contains the UV box electronics, controls and powers supply means (not shown). In UV box 500 the support is made by a series of liftable elongated transverse elements (bars) 501, 501', 501'', 501''' rotatably mounted on the base wall 510, where each of them has a conventional system (not shown) to lock/unlock them in place onto the base wall 510.

FIG. 5B shows in details a single liftable element 501 in its two positions, at "rest" represented by the dotted lines, and lifted in solid lines.

It is to be underlined that the present invention is not limited to any number of liftable elements, or specific materials or shapes, or to the transverse arrangement. With regards to liftable bar shapes, an interesting variant is shown in the partial front view of FIG. 5C, where support 5010 presents a recess 5011 useful to avoid rolling of cylindrical objects with narrower dimensions, e.g. thermometers.

Figure 6:
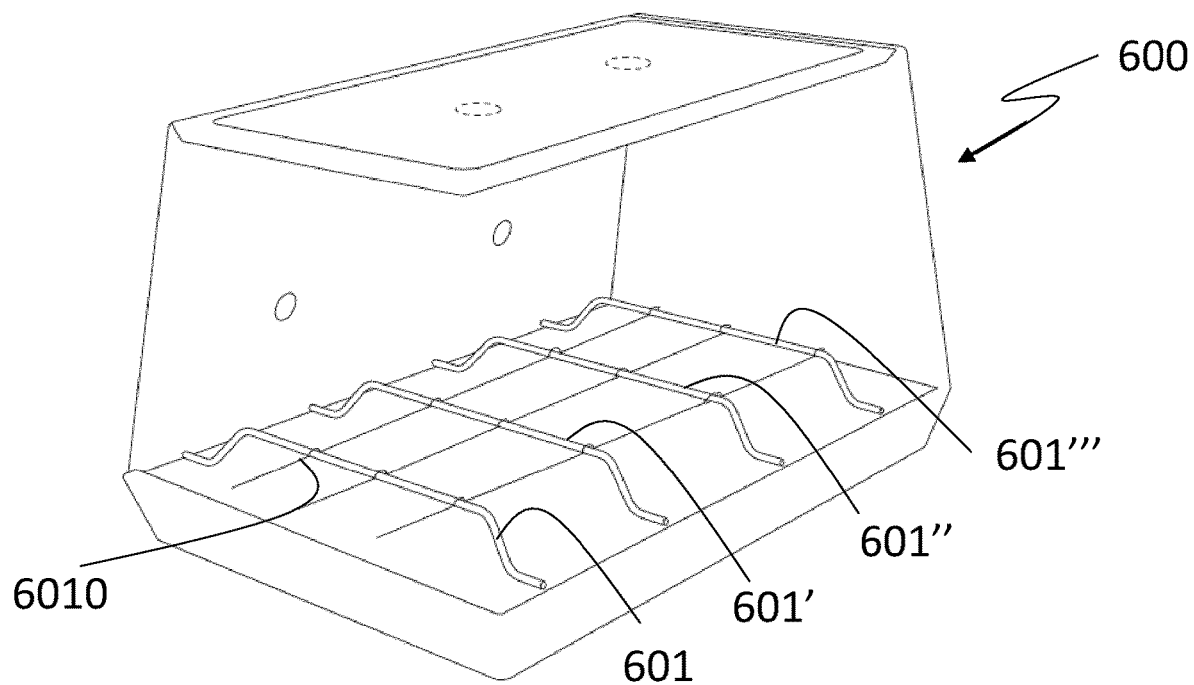
FIG. 6 shows a schematic representation of a UV box interior similar to FIGS. 5A-5C according to an alternate embodiment.

All the liftable elements may be controlled, i.e. lifted or lowered, separately or alternately they can be connected together in such a way that just lifting or lowering one of them, preferably the most easily accessible one such as the one closer to the opening wall, will result in also the other ones being moved to the lifted or lowered position. For example, as shown in the perspective view of FIG. 6, UV box 600 presents four liftable bars 601, 601', 601'', 601''' connected together by means of connecting rods 6010 rotatably fixed to the bars in any suitable way.

Finally it is to be underlined that, in this embodiment, the relation for the distance of the support from the base and upper walls of the UV box is to be measured from the lifted element portions that define the resting plane of the object(s) to be treated by UV radiation.

In a preferred embodiment the UV boxes are powered through rechargeable batteries, in a most suitable variant through one or more solar panels mounted on the external surface of the UV box walls. Optionally, a charge controller can be used to optimize the charge and discharge cycles.

The batteries, as well as any driving or control electronics with switches and user interface panels, may be elements separable from the UV box or more preferably can be permanently connected to the UV box, this latter solution being the preferable one in case of a foldable or assemblable UV box.

Optional elements advantageously present in the UV box according to the present invention are safety interlock switches to switch off the UV sources when the box is open, to avoid powering the box if it has not been properly assembled or if it is accidentally opened during the disinfection process. Also UV sensors or exposure meters may be present, even if they are of more marginal relevance.

The invention, its principles and advantages will be further illustrated by means of the following non-limiting examples.

EXAMPLE 1

Photometric measurements were carried out to determine the UV irradiance generated inside a foldable UV system with a rectangular parallelepiped shape and having disinfection volume dimensions of approximately 30 cm×15 cm×15 cm (L×W×H). The system was equipped with six UV sources powered by a cumulative electric power P of 3 W (ratio P/V=0.44 mW/cm$^3$), according to the configuration shown in FIG. 1. The walls were coated with highly UV-reflective porous-PTFE layers (Porex Virtek™ foils) 0.75 mm thick, and the UV sources were UV chips produced by LightLab Sweden AB with a UV output power of 10 mW each and generating radiation with an emission peak centered at 265 nm and a second lower peak centered at 305 nm. The UV irradiance inside the disinfection volume was measured by means of a UV sensor module UVM-30 A, suitable to have a good responsivity in the range 200-370 nm and calibrated, connected to a proper acquisition system.

The UV irradiance values measured in the central area of the system at a height of about 4 cm from the base with the sensor facing upwards in the direction of the upper UV sources were above 140 µW/cm$^2$. The UV irradiance values were also measured in the central area of the UV box by positioning the sensor over a UV-transmitting THV support 180 µm thick, with its sensitive area facing the box base, i.e. toward a surface with no active UV generation. This disposition reflects what happens to the surface of 3D objects not exposed to direct UV radiation but only to UV impinging thereon via (multiple) reflections onto the highly reflective inner surfaces of the walls.

Average values of UV irradiances measured for different distances of the support from the base and relative values of the same UV irradiances normalized to the highest measured value (116 µW/cm$^2$) are reported in table 1 below:

TABLE 1

| Distance from the box base (cm/% of the total height) | Measured UV irradiance with UV sensor facing the box base (µW/cm$^2$) | Relative values of the measured UV irradiances with respect to the maximum value |
|---|---|---|
| 0.2 cm/1.3% | 5.8 | 5 |
| 1.0 cm/6.7% | 34.8 | 30 |
| 1.7 cm/11.3% | 83.5 | 72 |
| 2.5 cm/16.7% | 104.4 | 90 |
| 4.0 cm/26.7% | 116.0 | 100 |
| 5.5 cm/36.7% | 109.0 | 94 |
| 7.0 cm/46.7% | 98.6 | 85 |
| 9.0 cm/60.0% | 74.2 | 64 |

It is possible to observe that only with the distance range specified by the present invention, namely having 0.1≤d1/(d1+d2)<0.5, relative UV irradiances higher than 70 are achievable, such value being defined as a threshold for UV box efficient systems, since lower values will result in a too low disinfection action brought by the reflected radiation. It is also possible to observe that UV systems according to the preferred embodiment, namely having 0.15≤d1/(d1+d2) ≤0.4, present a heightened efficiency, more specifically the relative UV irradiance is well above 85.

EXAMPLE 2

Photometric measurements were carried out to determine the UV irradiance created inside the same foldable UV system with rectangular parallelepiped shape and dimensions described in example 1, but with different placement of the UV sources as shown in FIGS. 4A-4E in UV system schematics C1, C2, S1, C3, S2.

A) Comparative example C1: six UV sources are placed on a single wall, the upper wall of the UV system, at equal distances between each other, with the main component of the emitted UV radiation orthogonal to both the mounting wall surface and the box base;

B) Comparative example C2: two series of three UV sources are mounted onto two adjacent walls, a side wall and the upper wall, in their median region to achieve equidistance from the wall edges, also in this case with the main UV radiation orthogonal to the mounting walls;

C) Sample S1: the UV sources positioning is the same of comparative example C2 but with the UV sources mounted on the side wall with a 10° inclination toward the base wall;

D) Comparative example C3: in this case three series of two UV sources are mounted onto three walls, the upper wall and the two adjacent side walls, and in each wall the UV sources are equidistant between each other and mounted onto the wall median region with their main emission orthogonal to the mounting wall;

E) Sample S2: the UV sources positioning is the same of comparative example C3 but with the UV sources mounted on the side walls with a 20° inclination toward the base wall.

The UV irradiance inside the system was measured by means of the same UV sensor module UVM-30 A and in the same way as in example 1. Then the UV irradiance was measured also by rotating the sensor 90° so that it faced the back wall and then the side wall where no UV sources were present, except in the case of configurations D) and E) where UV sources were present on both side walls but not directly in front of the sensor. Additional UV measurements were carried out by placing the UV sensor at 3.5 cm from the side wall without UV sources, in configurations B) and C), or from any of the side walls in configurations D) and E).

Average values of relative UV irradiances measured for the different configurations (normalized to the highest value) are reported in table 2 below.

TABLE 2

| Ref. | Relative UV irradiance towards the base wall | Relative UV irradiance towards the side wall (sensor in the box center) | Relative UV irradiance towards the side wall (sensor at 3.5 cm from the side wall) | Relative UV irradiance towards the back wall |
|---|---|---|---|---|
| C1 | 96 | 70 | 65 | 67 |
| C2 | 93 | 79 | 78 | 78 |
| S1 | 95 | 85 | 79 | 80 |
| C3 | 89 | 99 | 98 | 82 |
| S2 | 94 | 100 | 98 | 84 |

It can be seen from the above relative values that configurations with sources on multiple walls are better than the one with single wall mounting (comparative example C1) to have a more homogeneous distribution of the reflected radiation in all the directions. In addition, it has to be remarked that in case the objects to be disinfected are bulky, the mounting of UV sources on a single wall will result in a massive shadow effect induced by the object that will significantly reduce the reflected radiation.

Furthermore, the configurations with the sources distributed on more walls (three walls as in D and E) are better than the configurations with the sources distributed on less walls (two walls as in B and C), and in any case the tilting of the UV sources on the side walls to create angles of 70°-80° between their main emission direction and the main emission direction from the UV sources mounted on the upper wall is suitable to improve the intensity of reflected radiation. In fact, as shown by the direct comparison between the results obtained with the same type of configuration, comparative example C2 is worse than sample S1 and comparative example C3 is worse than sample S2.

It was found that for angles lower than 60°, i.e. UV sources mounted on the side walls with more than a 30° inclination toward the base, the additional advantages on the reflected radiation are not significant.

EXAMPLE 3

Additional photometric measurements were carried out with the UV system configuration of sample S1 with different reflective coating layers:
a) Aluminum reflective sheets with average reflectance in the UV region close to 90%;
b) 0.75 mm thick porous-PTFE layers (Porex Virtek™ foils) with average reflectance in the UV region of 94%.

The UV irradiance was measured as in example 1, and the average value of relative UV irradiance was 7% lower for coating a) with respect to coating b).

The best coating is therefore represented by the 0.75 mm thick highly reflective porous PTFE, and preferred coating thicknesses are comprised in the range 0.20-1.50 mm.

It has been verified that high purity (>99.9%) metal coatings of thickness up to 500 nm, made for example through sputtering, are suitable to improve the UV reflectance of aluminum; for this purpose and effect, Al and Ag are the preferred metals.

EXAMPLE 4

A system made according to the second embodiment of the present invention, namely a system, defined as sample S3 with trapezoidal cross-section having dimensions of the base wall 22 cm×30 cm, of the upper wall 15 cm×30 cm, and height of about 14 cm has been evaluated and compared with commercially available systems with UV sources just on the upper wall and standard Al surfaces with reflectance <80%. The main features of the S3 system and of the commercially available ones, comparative samples C4-C6, are highlighted in table 3 below, while their performances intended as the time required to achieve a 99.9% disinfection level, are reported in table 4 below.

TABLE 3

| Sample ref. | Inner volume V (cm$^3$) | Number and type of sources | Cumulative electric power P (W) | P/V ratio (mW/cm$^3$) |
|---|---|---|---|---|
| S3 | 7750 | 6 UV-C chips | 3 | 0.39 |
| C4 | 1590 | 8 UV-C LEDs | 8 | 5.03 |
| C5 | 7020 | 24 UV-C LEDs | 8 | 1.14 |
| C6 | 2060 | 4 UV-C LEDs | 4.3 | 2.09 |

TABLE 4

| Sample ref. | Disinfection time |
|---|---|
| S3 | <2 min |
| C4 | 3 min |
| C5 | 3 min |
| C6 | 8 min |

It is possible to observe that not only the system according to the present invention is the fastest one, but even though it has the biggest inner volume it requires a cumulative power less than a half with respect to the one of comparable size (C5), rendering it the most efficient system with the lowest Power per unit Volume (P/V) ratio.

The above examples each explore the effect of a specific feature of the UV box of the present invention, even though it is their concurrent presence and synergistic effect that allows to achieve a UV disinfection box system with enhanced characteristics with respect to the ones of the prior art.

The invention claimed is:

1. A box-shaped UV disinfection system having plural walls including a displaceable wall capable of opening and closing said system, said system further comprising a plurality of discrete UV sources disposed on said walls and an internal UV-transmitting support, wherein all of the internal wall surfaces have a reflectance higher than 80% in the wavelengths range between 250 and 350 nm, said discrete UV sources are disposed on at least two of its walls that are adjacent to each other, and said UV-transmitting support has at least a 70% UV transmittance in the wavelengths range between 250 and 350 nm and is located at a minimum distance d1 from a base wall and at a maximum distance d2 from an opposite upper wall such that $0.1 \leq d1/(d1+d2) < 0.5$, wherein the discrete UV sources disposed on at least one of the walls are inclined towards the base wall with an angle comprised between 5° and 30°, and wherein the discrete UV sources are not present on at least one of the base wall and the displaceable wall.

2. A box-shaped UV disinfection system according to claim 1, wherein the UV-transmitting support is held on at least two different walls, or is held by pillars in contact with the base wall.

3. A box-shaped UV disinfection system according to claim 1, wherein the UV-transmitting support is a netted structure with a void-to-fill ratio comprised between 3 and 200.

4. A box-shaped UV disinfection system according to claim 1, wherein the UV-transmitting support is made with a UV-transparent material chosen from a terpolymer of tetrafluoroethylene, hexafluoropropylene and vinylidene fluoride, ethylene tetrafluoroethylene, and UV-transmitting synthetic glass.

5. A box-shaped UV disinfection system according to claim 1, wherein the support comprises a series of parallel liftable and lowerable elements rotatably mounted on the base wall and connected through connecting elements such that all said parallel liftable and lowerable elements can be lifted and lowered by acting on one of them only.

6. A box-shaped UV disinfection system according to claim 1, wherein the internal wall surfaces are made of or coated with porous PTFE or aluminum layers with nanometric coating of a metal.

7. A box-shaped UV disinfection system according to claim 1, wherein the inclination of the discrete UV sources is obtained by mounting them inclined with respect to the wall on which they are mounted.

8. A box-shaped UV disinfection system according to claim 1, wherein the inclination of the discrete UV sources is obtained by the inclination of the wall on which they are mounted.

9. A box-shaped UV disinfection system according to claim 8, wherein the box cross-sectional shape is trapezoidal.

10. A box-shaped UV disinfection system according to claim 1 wherein it has an inner volume V comprised between 2000 and 14000 $cm^3$ with a ratio of the cumulative electric power P of the discrete UV sources to the inner volume V comprised between 0.25 and 0.60 $mW/cm^3$.

11. A box-shaped UV disinfection system according to claim 1, wherein the discrete UV sources are UV-C LEDs or chips with a spectral emission with a first peak in the range 260-280 nm and a second peak in the region 290-310 nm.

12. A box-shaped UV disinfection system according to claim 1, wherein the number of discrete UV sources is six, distributed evenly on two or three walls.

13. A box-shaped UV disinfection system according to claim 1, wherein the walls are connected such as to allow unfolding of the box with a ratio between an inner volume V and a volume of the unfolded box comprised in the range 4-16.

14. A box-shaped UV disinfection system according to claim 1, wherein it further includes a solar panel on the outside surface of at least one of the walls, said solar panel being optionally connected to an energy storage rechargeable battery.

15. A box-shaped UV disinfection system according to claim 1, wherein it further includes a separate power supply module suitable for coupling with the discrete UV sources.

16. A box-shaped UV disinfection system according to claim 1, wherein a power supply module for the discrete UV sources and other electronic components are embedded in the system outside an inner volume V.

17. A box-shaped UV disinfection system according to claim 16, wherein the power supply module and other electronic components are contained in a container coupled to the base wall or forming the base wall.

18. A box-shaped UV disinfection system according to claim 1, wherein it further includes one or more safety interlock switches suitable to switch-off the discrete UV sources when the box is opened or to prevent their powering if the box is not properly assembled.

19. A box-shaped UV disinfection system according to claim 1, wherein the discrete UV sources are not present on the base wall.

20. A box-shaped UV disinfection system according to claim 1, wherein the discrete UV sources are not present on the displaceable wall.

* * * * *